United States Patent
Paskalov

(10) Patent No.: US 7,718,120 B2
(45) Date of Patent: May 18, 2010

(54) RF PLASMA SYSTEM FOR MEDICAL WASTE TREATMENT

(76) Inventor: George Paskalov, 22002 Linda Dr., Torrance, CA (US) 90503

(*) Notice: Subject to any disclaimer, the term of this patent is extended or adjusted under 35 U.S.C. 154(b) by 0 days.

(21) Appl. No.: 11/999,282

(22) Filed: Dec. 6, 2007

(65) Prior Publication Data
US 2008/0247904 A1 Oct. 9, 2008

Related U.S. Application Data

(60) Provisional application No. 60/874,001, filed on Dec. 11, 2006.

(51) Int. Cl.
*A61L 2/14* (2006.01)
(52) U.S. Cl. .................. 422/28; 422/22; 422/184.1; 241/15
(58) Field of Classification Search .......... 422/22, 422/28, 184.1, 309; 241/15
See application file for complete search history.

(56) References Cited

U.S. PATENT DOCUMENTS 5,252,290 A * 10/1993 Uesugi .................. 422/22
5,876,663 A * 3/1999 Laroussi ................. 422/23
7,022,293 B2 * 4/2006 Hogan .................. 422/184.1

* cited by examiner

*Primary Examiner*—Sean E Conley
(74) *Attorney, Agent, or Firm*—Fish & Associates, PC

(57) ABSTRACT

A system and method are provided for the thermal and non-thermal (oxidation) plasma treatment of medical waste using an electrode-less induction (thermal) and capacitive (non-thermal) plasma torches. The medical waste is pre-treated by liquid nitrogen, crushed and pulverized by LN2 crusher/pulverizer, and conveyed to the nitrogen/water thermal plasma reactor, which converts the powdered medical waste into carbon black and generated gas (resulting from the thermal step) is directed to the Oxygen non-thermal plasma reactor for post-treatment. The system is equipped with an emission control unit, dual frequency pulse RF power supply, and Liquid Nitrogen Generator. The off gas from LN2 crusher (nitrogen) is used for the induction plasma torch and off gas from LN2 generator (oxygen) is used as a plasma gas for the Non-thermal plasma torch.

10 Claims, 4 Drawing Sheets

General Diagram

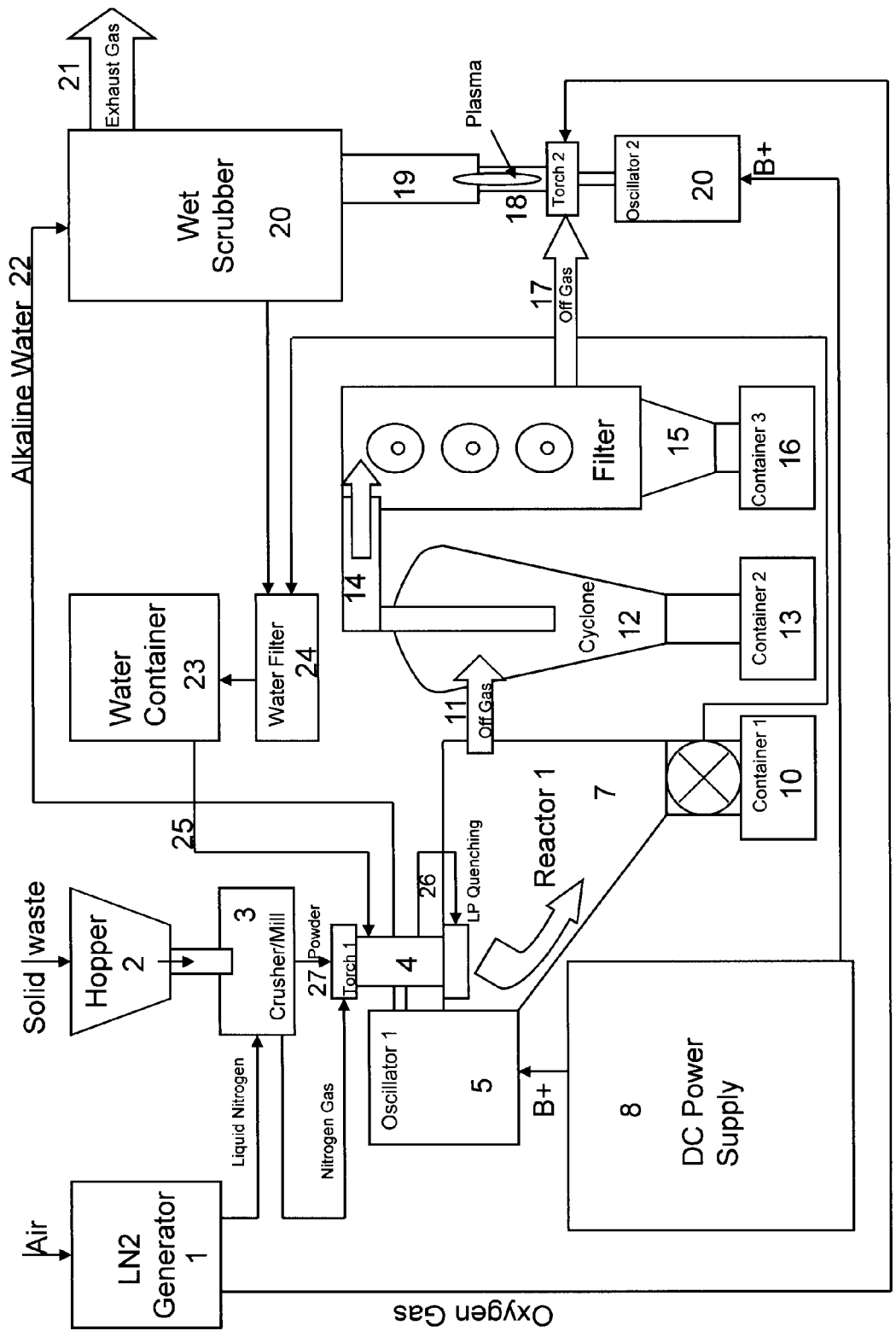
Fig.1 General Diagram

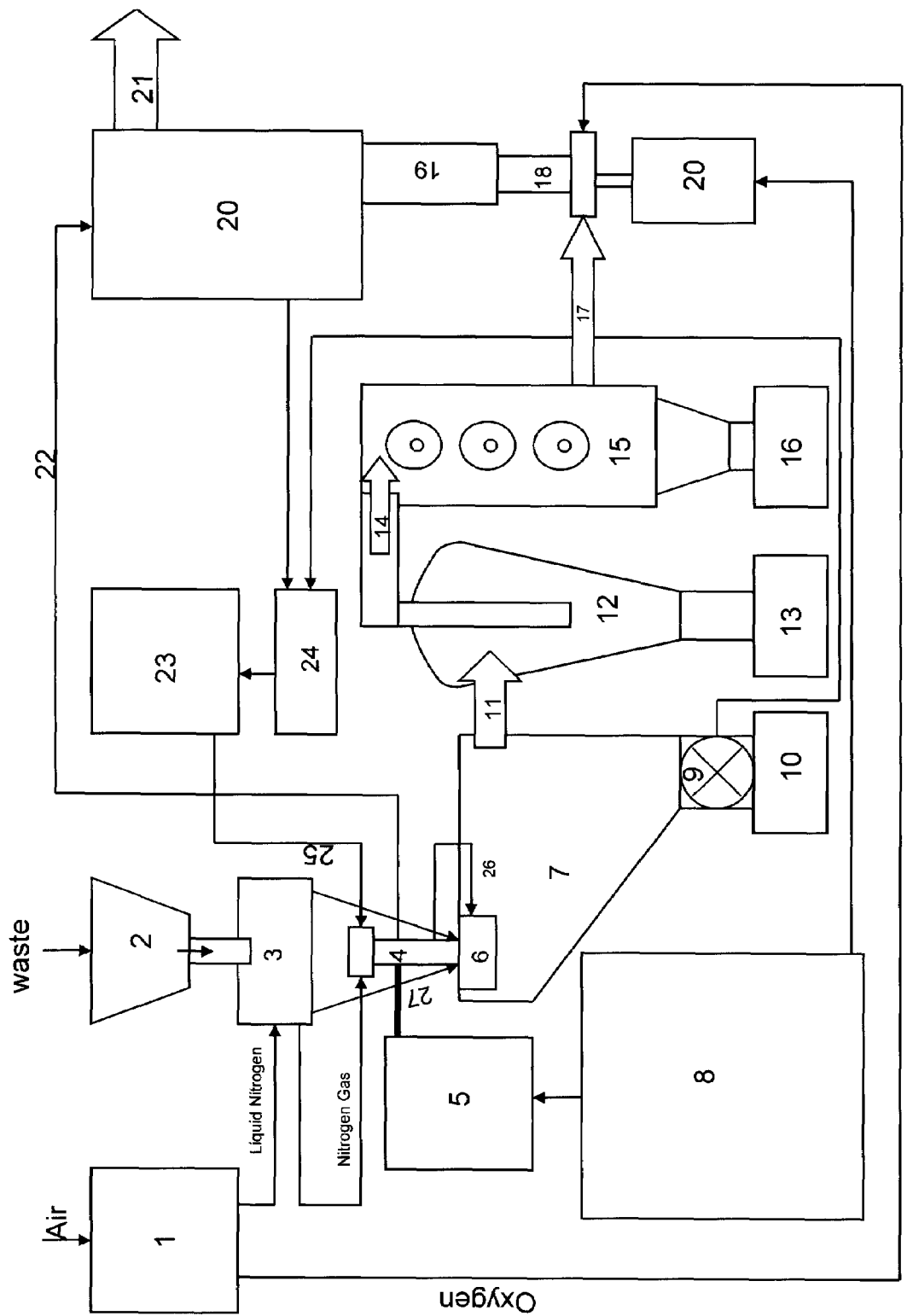
Fig.2 Vertical Configuration

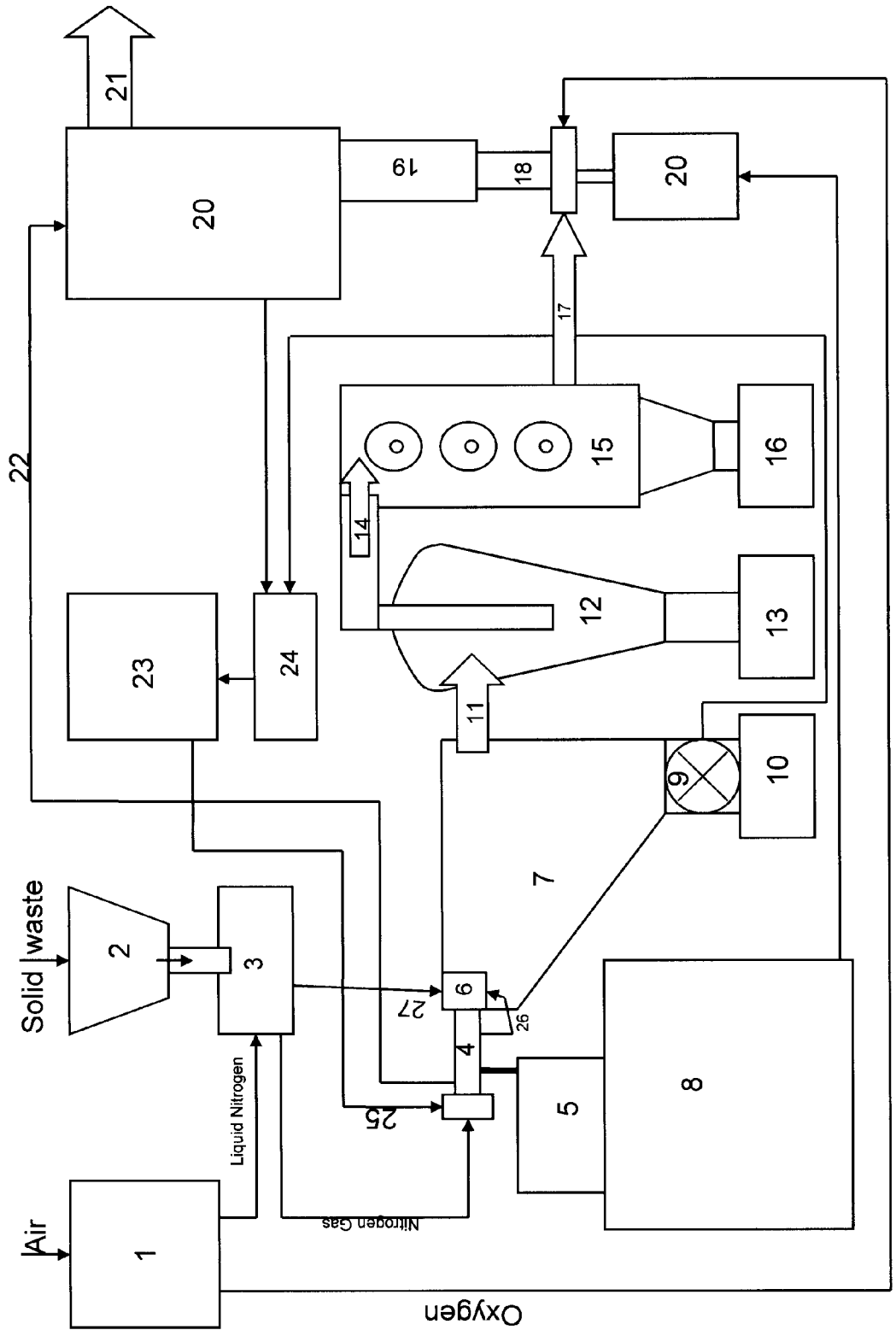
Fig.3 Horizontal Configuration

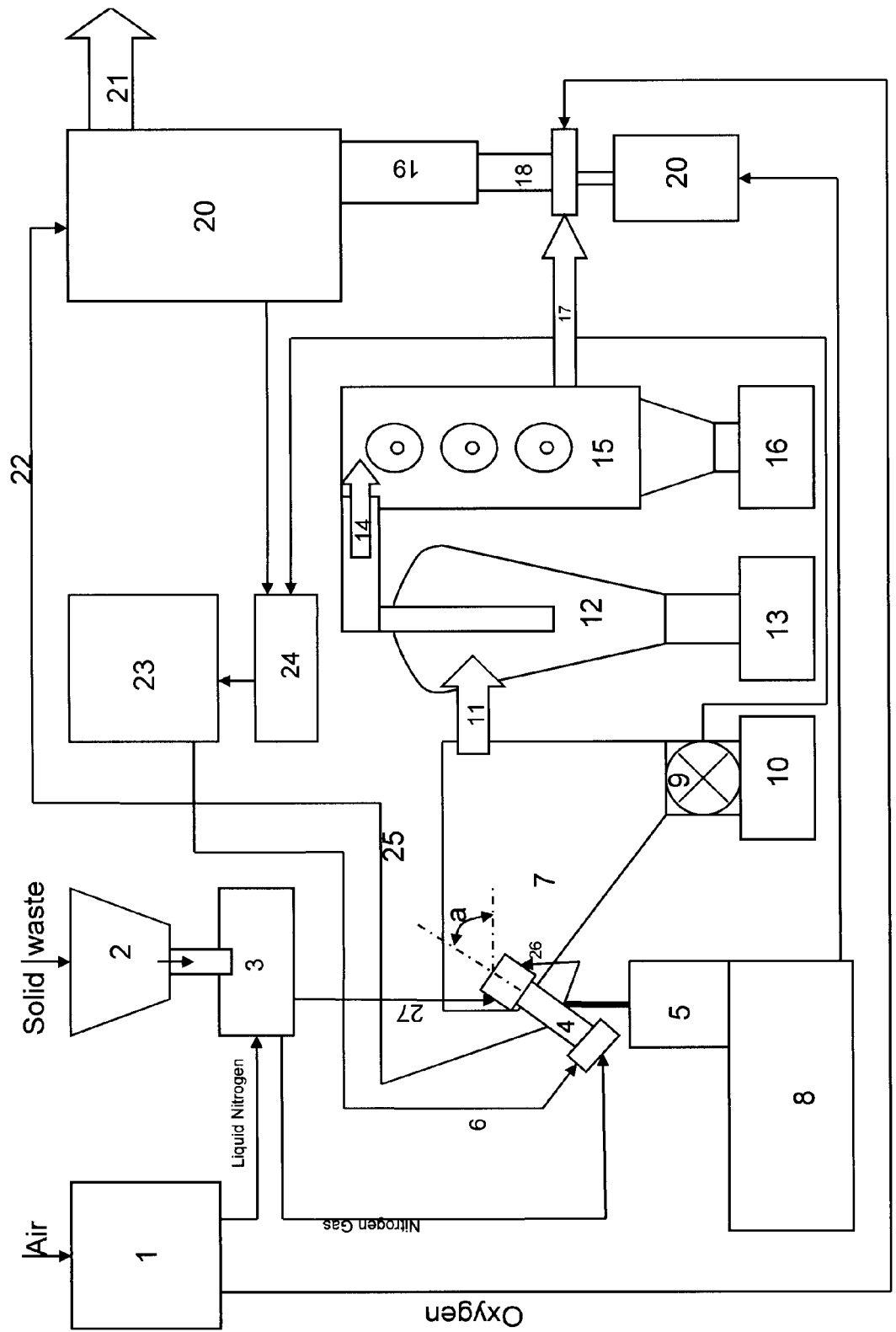
Fig.4 Combined Configuration

RF PLASMA SYSTEM FOR MEDICAL WASTE TREATMENT

CROSS-REFERENCES TO RELATED APPLICATION

This application claims the priority benefit of U.S. Provisional Application Ser. No. 60/874,001 filed Dec. 11, 2006.

FIELD OF THE INVENTION

The instant invention relates to an apparatus and method for converting hazardous medical waste to safe, non-hazardous material, and more particularly to such process conducted in a plasma environment.

BACKGROUND

This invention relates to the destruction of hazardous hospital waste and, more particularly, to the destruction of hazardous medical waste using an electrode-less radiofrequency inductive and capacitive plasma discharges in combination with cryogenic material pre-treatment. The processing method includes breaking up the medical waste into powder using liquid nitrogen crusher/mill, exposing the medical waste in powder form to thermal RF plasma, and converting the disinfected powder into compact form. The term medical waste encompasses not only medical waste, but also veterinary waste.

A major problem facing modern society is the disposal of hazardous medical waste materials in a manner which is capable of reducing hazardous waste to compounds suitable for environmental disposal. Such suitability is, of course, defined in terms of acceptable levels of pollutants as determined by regulatory agencies. For example, regulated medical waste consists of the following categories: pathological waste; blood and blood product; contaminated "sharps", such as needles, syringes, scalpels, blades, and broken glass; animal waste; cultures and stocks of infectious agents and associated biological; and disposable products, such as gloves. Commercial medical waste treatment technique includes steam sterilization (autoclaving), incineration and chemical disinfection. A number of attempts have been made in the prior art to destroy medical waste using microwave, RF direct heating, direct current arc discharge plasma source and RF plasma source.

Incineration of medical waste, while it does effectively sterilize it, has other consequences that can be extremely detrimental to public health. One of these is the production and emission of dioxin. The medical waste consists approximately 15% of plastic, most of which is chlorinated, such as PVC, which is more than 50% chlorine by weight. When plastic is incinerated in the presence of carbon and oxygen, it creates dioxin—considered the most carcinogenic compound known. Incinerators emit pollutants at very high rate, such as cadmium, arsenic, lead, dioxins, and furans. Emissions from these incinerators may be a bigger public health threat than improper dumping.

The autoclave (steam sterilizer) has been used in medicine to sterilize medical instruments. Similar systems are used for medical waste treatment. Typically medical waste is directed to a sealed chamber, to which steam is fed at approximately 160 degrees C., and pressure range between 100 to 500 kPa. Treatment time vary from 30 to 100 minutes. The process is simple, easy to control, and efficient against most of the microorganisms. However, the autoclaving has several drawbacks: it is expensive and time consuming; and it is not recommended for the treatment of organic solvents and reagents, as well as chemotherapy, pharmacological and pathological waste.

The idea of microwave treatment of medical waste originated in Germany in the early 1980 s, and since then it has been used in many countries. The sanitation process uses steam pre-heating with the help of microwaves. Medical waste material is shredded and granulated. After that the waste is humidified by hot steam and moved to a waste treatment chamber for 20-30 minutes (see for example, U.S. Pat. Nos. 5,223,231; 6,830,662B2). The system is totally closed, and therefore it does not cause any emissions. But the processed waste (disposal) still contains organic material, which could generate methane and other toxins during the landfill storage. Also, the microwave technology cannot be used in the case of liquid blood and hazardous chemicals and drugs.

None of these approaches have proven acceptable, due to the fact that materials released to the environment remain as unacceptable sources of pollution ([1] Alternative medical waste treatment technologies approved by California Department of Health Services, Medical waste management Program, MS7405, Jun. 18, 2004). Only plasma systems could be use to process all kinds of medical waste. Other technologies are limited.

One such attempt is disclosed in U.S. Pat. No. 7,216,593B2. This reference teaches the use of DC and/or AC plasma torches with a variable flame mounted with the vessel. The waste is introduced into the vessel in the form of solid pieces, preliminary treated by disinfectant. The plasma melts or vitrifies the inorganic portion of the waste and gasifies and dissociates the organic portion of the waste. The disadvantages of the above system are: it requires disinfectant for pre-treatment; a molten bath is necessary in order to make the system efficient, but at the same time the presence of the molten bath makes the system very inertial and increases the probability to generate dioxins at a very high rate, especially during the start-up and shut-off; and there is a high capital cost. The U.S. Pat. No. 6,551,563B1 teaches us method and systems for safely processing hazardous waste, including medical waste. The system is based on pyrolysis and includes a torch, vessel, scrubber, feeder thermal oxidizer and gas supply unit. The disadvantages of the system are that requires a separate gas supply unit and there is a short life time of the arc plasma's electrodes, due to the aggressive plasma environment (chlorine; HCl, etc.).

U.S. Pat. No. 5,762,009 teaches us plasma energy recycling and conversion (PERC) reactor and process for disposal of waste using induction coupled plasma heat source and two reaction chambers. Argon is used to create the plasma jet and convert waste to a gas.

The U.S. Pat. No. 5,943,970 teaches us the method and equipment for waste thermal destruction on the surface of the bath of melted metal. The reliable destruction of bacteria is provided, but dioxin and furans are generated, especially during system start-up and shut-off.

The integrated plasma-frequency induction process for waste treatment is described in (WO/2004/048851 Blush Wizoso Integrated Plasma-Frequency Induction Process for Waste Treatment, Resource Recovery and Apparatus for Realizing Same, Oct. 6, 2004), and is based on combined simultaneous plasma arc and direct induction heating of preliminary briquetted waste. They use oxygen injection to the molten pool and quench the synthetic gas after reactor. The drawbacks are that the presence of oxygen dramatically increases the emission of dioxin, and the efficiency of induction heating is very sensitive to the chemical composition of the medical waste. Many experimental data shows that pyrolytic destruction of hazardous waste generates flammable and potentially explosive gases, such as hydrogen and carbon monoxide, making the pyrolytic systems unsafe to operate. Because medical waste comprises a combination of different substances (plastic, glass, fabrics, etc.) and is not consistent from day by day, it is very difficult and expensive to control the oxygen/hydrogen ratio, i.e. the system could easy exceed safe levels.

The prior art plasma medical waste treatment systems suffer from a variety of shortcomings, which have prevented their widespread use in commercial applications. One shortcoming results from the fact that the waste material generally cannot be introduced directly into a plasma arc, because such introduction causes contamination of the electrodes and subsequent erratic operation of the arc. The same things happen when material is introduced directly into RF plasma discharge. The performance of the arc plasma is highly sensitive to the waste composition and flow rate. Arc electrode erosion further complicates the maintenance, operation, and stability of the system. Small scale operation of DC arc plasmas is also very inefficient due in part to the minimum gas flow rate and electric power requirements needed to strike and sustain the arc. Scaling the prior art systems for operation with different medical waste composition has proven to be difficult, requiring major system configuration changes, which are expensive to accomplish.

In summary, none of the prior art systems have provided an apparatus and method of efficient medical waste treatment to prevent pollution from medical waste, and reduce hazardous medical waste to components suitable for environment disposal.

SUMMARY OF THE INVENTION

A system and method are provided for the destruction of hazardous medical waste material using electrode-less induction and capacitive coupled RF plasma in combination with cryogenic pre-treatment of the waste. The medical waste material, packed in leak- and puncture-resistant containers, is delivered into a liquid nitrogen crusher/mill module. The cryogenic grinding system is based on liquid nitrogen. Pre-crushing energy is reduced as liquid nitrogen causes the feed material to become brittle. The medical waste can then be easily pulverized using a simple mechanical mill. The mill operates at temperatures down to −80 degrees C. at the mill exit, with the throughput capacity between 5 and 100 kg/hr. The particle size ranges between 100 and 600 microns which is small enough to be efficiently processed in the plasma stream. The cryogenic system consists of an air compressor, air dryer, PSA-gas separation and cryogenic generator (liquefier). Air is separated for nitrogen and oxygen. Nitrogen is used in the liquefier to make liquid nitrogen. Oxygen typically is wasted, but is used in our system as a plasma gas for the non-thermal capacitive plasma torch. After medical waste was exposed to the liquid nitrogen, the evaporated Nitrogen gas is use as a plasma gas for thermal induction plasma torch. The stainless steel double-wall reactor is water cooled, and lined with ceramic tiles. Container 1 collects processed solid waste. The powder is heated by a plasma stream and rapidly quenched by low pH water (LP quenching), in order to decrease the particle temperature from melting point to room temperature, and avoid dioxin formation. Low pH water is generated from tap water by passing the plasma torch chamber (G. Paskalov et al. U.S. Pat. No. 7,291,314B2, 2007). The commercial feeding system was modified in order to produce a continuous feed of the medical waste in powder form. The cyclone is water cooled and equipped with the additional fan to optimize the separation efficiency. Container (2) collects the coarse powder. Container (3) collects fine powder. A bag house filter is equipped with the reverse air-jet, a PLC controller, a differential pressure sensor, and carbon filters. The off gas is directed to the Torch 2 (capacitive coupling RF plasma) for oxidation in plasma reactor 2. A wet scrubber cleans the final gas before it is exhausted.

One aspect of the present invention relates to a method of processing medical waste, which includes the steps of continuously feeding medical waste into a liquid nitrogen crushing module and exposing the crushed material (powder) passing the thermal plasma stream in-flight, so as to heat and disinfect the solid medical waste, quenching the product, and off gases are mixed with the oxygen and are processed by the non-thermal capacitive plasma torch, before exhaust.

A second aspect of the present invention is to use liquid nitrogen vapor as a plasma gas for thermal plasma, and "waste" oxygen as a plasma gas for non-thermal plasma.

A third aspect of the present invention relates to a method of rapidly quenching the processed material using low pH water in order to avoid toxic gas generation.

Each aspect of the present invention provides an efficient apparatus and method to reduce (destroy) the infectious potential of medical waste and to transform it into material which would not adversely impact the overall environment. The present invention provides improved throughput of medical waste per unit volume in addition to improved reduction of toxic gas exhaust. Each aspect of the present invention also provides improved thermal performance by using a thermal induction plasma torch for in-flight treatment of solid particles and non-thermal capacitive plasma for off-gas treatment.

Additional advantages and novel features of the invention will be set forth in part in the description and to those skilled in the art upon examination of the following or may be learned by practice of the invention.

DETAILED DESCRIPTION

Referring to FIG. 1, there is shown a block diagram of a medical waste destruction (treatment) system, constructed in accordance with the present invention.

1. Disintegrating and Shredding the Medical Waste.

Medical waste in sealed boxes arrives at the medical waste treatment unit and is unloaded onto a conveyor belt, where all boxes are counted. The load conveyor carries the medical waste into the sealed hopper (2) and liquid nitrogen crusher/mill (3), which is designed to disintegrate medical waste into powder at cryogenic conditions (for example, Hosokawa Alpine Countraplex 160C). As herein defined, disintegration refers to breaking up, shredding and crushing material to a relatively uniform size that is in the range of 100 to 600 microns. The liquid nitrogen crusher/mill module has several features to prevent the escape of contamination from the hopper. First entry is controlled by two sets of airlocks: inlet and outlet, i.e, two sets of doors. The first one is open to allow medical waste going to the hopper. After the first door is closed, the second one is opened and permits the material to enter the crusher/mill. The disintegration or shredding is performed by a cryogenic grinding system based on liquid nitrogen. Pre-crushing energy is reduced as liquid nitrogen causes the medical waste to become brittle, allowing the mill to achieve high levels of grinding performance. Additionally, the inert gas atmosphere within the mill provides a high degree of safety. The mill operates over a temperature range down to −80 degrees C. Throughput capacity is between 5 and 150 kg/hr with a particle size range between 100 and 600 microns.

2. Liquid Nitrogen Generator (1).

The Liquid Nitrogen Generator (PCI90) produces liquid nitrogen using atmospheric air as the feed stock. Atmospheric air is compressed, purified, cooled, separated and the purified liquid nitrogen is delivered to the crusher/mill unit. The "waste" oxygen is collected, compressed, and delivered to the secondary plasma torch.

3. Feeding System (27).

The medical waste in powder form enters the feeding system, which includes a feed conveyor and digital feeder (for example, K-Tron model 304 Dual Drive). The feeding system delivers the medical waste powder to the plasma reactor (7). A small amount of carrier gas is applied.

4. Reactor (7).

The reactor includes a thermal plasma torch (4), reactor itself (7), airlock valve (9), container (10), and off gas exhaust pipe (11).

5. RF Induction Plasma Module

The RF Induction Plasma Module includes a DC Power Supply (8), oscillator (5), and induction plasma torch (4). The oscillator working frequency is in the range of 60 kHz to 5 MHz. The temperature within the plasma stream of the induction plasma torch is normally greater than 2700 degrees C., typically at least about 3900 degrees C., and usually about 4800 to 5300 degrees C. range; with temperatures in excess of about 6400 degrees C. being acceptable for usage in the inventive process. Plasma having temperatures effective for the present purpose may be generated by any suitable radio-frequency induction plasma torch. The reaction pressure may vary widely and may be sub-atmospheric, atmospheric or super-atmospheric; typically atmospheric for ease of operation. The medical waste feed rate to the plasma stream is not a critical aspect of the inventive process. Typically, and depending upon the particular torch being employed, the rate at which the medical waste is introduced as a powder into plasma environment or stream, is generally in the range of from 5 kg/hr to 550 kg/hr, usually between 10 to 150 kg/hr. Depending upon the temperature of the plasma stream and medical waste flow, the processing time of the medical waste powder within plasma zone can be relatively short. Processing time is the time needed to heat the material higher than 700 degrees C. This temperature is enough to destroy any kind of bacteria and viruses, but prevent dioxin formation. In general, the higher the temperature the shorter the residence time; normally in the range of about $1 \times 10^{-1}$ second to $1 \times 10^{-5}$ second, typically $1 \times 10^{-2}$ to $1 \times 10^{-3}$ second. By employing suitable combinations of medical waste feed rate, plasma temperature and processing time, the inventive process can be tailored to obtain an optimal result. In other embodiments of the invention, a product, which was obtained by cooling or quenching of plasma processed powder, can be separated into solid and gas components. By "quenching" it is meant that the plasma stream is cooled at rate of at least about $1 \times 10^3$ K/sec, e.g. from $1 \times 10^3$ to $1 \times 10^5$ K/sec. The plasma processed material is quenched by atomized low pH water (26). Low pH water (26) is produced from tap water (23) by passing the plasma torch chamber (4) (as described in U.S. Pat. No. 7,291,314B2, 2007). High pH water flow (22) is used as a reagent for the wet scrubber (20). The processed material drops to the bottom of the reactor and moves to the container 1 through airlock valve (9). Off gas includes plasma gas, generated gas, and waste vapor. The exhaust is directed to the cyclone (12), which removes coarse particles from off-gas. Coarse particles are collected in container 2 (13). The output of the cyclone is connected to a respective dust transfer duct (14) that feeds into the dust controller unit (15). The dust control unit preferably includes three filter stages: a continuous cleaning dust filter, a HEPA pre-filter, and a charcoal filter. These filters remove particulates from the gas stream. The effectiveness of the various air control devices is preferably: for dust filter 90% removal of particles bigger than 10 microns; HEPA pre-filter 95%>5 microns; charcoal filter 99.999%>0.12 microns. Off gas (17) is directed to the secondary torch (18)—non-thermal RF capacitive plasma oxidizer. Waste oxygen from the liquid nitrogen generator (1) and off gas (17) is mixed together and acts as a plasma gas for the secondary torch (18). The RF Capacitive plasma module includes a DC Power supply (8), oscillator (20) and capacitive plasma torch (18). The oscillator working frequency is in a range from 13.56 MHz to 150 MHz. Capacitive plasma discharge, which is generated by the secondary plasma torch (18), is known as a non-thermal plasma [G. Paskalov RF and Microwave plasma Torches, Novosibirsk, Nauka, 1992], i.e, the electron temperature is not equal to the ion temperature. Typically, the electron temperature is around 14,000 K, but ion temperatures just 1200 K. The Capacitive plasma torch is able to work at a very high gas flow rate, which makes the secondary torch very efficient as the oxidizer. The exhaust gas from secondary reactor (19) is directed to wet scrubber (20) for final gas cleaning. Clean gas (21) is exhausted to the atmosphere.

A few different configurations of the plasma reactor are presented on FIG. 2-4.

BRIEF DESCRIPTION OF THE DRAWINGS

FIG. 1 presents a block diagram of a medical waste destruction (treatment) system, constructed in accordance with the present invention.

FIG. 2 presents a vertical plasma reactor. The induction plasma torch is located on the top of the reactor. Medical waste powder is fed into the plasma stream at the end of the torch.

FIG. 3 presents a horizontal plasma reactor, where the induction plasma torch is attached to the reactor from the side. The feed material is transported into the plasma jet at a 90 degrees angle. This configuration permits higher heat exchange between powder and plasma.

FIG. 4 presents the combined configuration, where the induction plasma torch is attached to the reactor at a variable angle. The angle could vary in the range from 30 to 60 degrees, but preferably is 45 degrees.

EXAMPLE

Mixed medical waste was shredded and pulverized using the Hosokawa Liquid Nitrogen mill. Average particle size of the powder was about 100 microns. The powder was delivered into the induction plasma jet by using K-Tron feeding system at feed rate about 45 kg/hr. Plasma power was 55 kW at working frequency 2 MHz. Plasma temperatures is developed by varying the discharge power and Nitrogen gas flow rate. Quenching device was designed in order to atomize low pH water and deliver it to the plasma reactor. Quenching rate was about $3 \times 10^3$ K/sec. The solid part of the processed material was collected in Container 1 and consists of 95% of total feed waste. The rest of the processed material was collected in Containers 2 and 3. Off gas from the filter unit was mixed with oxygen at ratio 1:1, and processed in capacitive plasma module with the following parameters: plasma power—10 kW;

frequency—13.56 MHz; gas flow rate—20 m³/Hr; Torch configuration: co-axial. Cylindrical electrodes were made from electrolytic copper.

The results of the medical waste plasma treatment are presented in the following table:

|  |  | Control Time | | | | |
|---|---|---|---|---|---|---|
| Influent, Pfu/ml | Organism | 30 sec | 5 min | 1 hour | 24 hours | 168 hours |
|  |  | Effluent, pfu/ml | | | | |
| 12,000 | *Bacillus Subtilis* | 0 | 0 | 0 | 0 | 0 |
| 1,500,000 | *E-coli* | 0 | 0 | 0 | 0 | 0 |
| 3200 | Rota &Polio Viruses | <0.1 | <0.1 | <0.1 | <0.1 | <0.1 |

Pfu/ml - Plaque Forming Units per Milliliter

The following is claimed:

1. A process for medical waste treatment, which comprises the steps of:
   a. Pulverizing medical waste into powder form;
   b. Generating a thermal plasma by the use of a Radio-Frequency plasma generating means;
   c. Introducing powdered medical waste into said thermal plasma, wherein said powder is heated to a temperature, sufficient to disinfect the medical waste and resulting in a processed powder;
   d. Cooling the processed powder;
   e. Generating non-thermal plasma, by the use of capacitive radio-frequency plasma generating means;
   f. Introducing exhaust gas resulting from step (d) into said non-thermal plasma wherein said gas is oxidized;
   g. Compacting the processed powder to form pellets.

2. The process of claim 1, wherein the medical waste is pulverized by a cryogenic crusher and mill.

3. The process of claim 2, wherein the medical waste is blended with liquid nitrogen.

4. The process of claim 1, wherein the thermal plasma is generated by an induction plasma torch.

5. The process of claim 1, wherein the non-thermal plasma is generated by a Radio-Frequency Capacitive plasma torch.

6. The process of claim 1, wherein the powdered medical waste is continuously fed into a plasma reactor comprising:
   a. A thermal plasma zone;
   b. A cooling zone downstream of said plasma zone adapted to quench the processed powder.

7. The process of claim 6, wherein the reactor is under atmospheric pressure.

8. The process of claim 6, wherein the processed powder is quenched by using water.

9. The process of claim 4, wherein source of plasma gas is a vapor of liquid nitrogen.

10. The process of claim 5, wherein source for plasma gas is the mixture of waste oxygen from Liquid Nitrogen Generator and off gas from thermal plasma reactor.

* * * * *